(12) United States Patent
Hoshiya et al.

(10) Patent No.: US 12,281,075 B2
(45) Date of Patent: Apr. 22, 2025

(54) METHOD FOR PRODUCING FLUOROVINYL AMIDE COMPOUND

(71) Applicant: DAIKIN INDUSTRIES, LTD., Osaka (JP)

(72) Inventors: Naoyuki Hoshiya, Osaka (JP); Motoshi Matsui, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 912 days.

(21) Appl. No.: 17/299,602

(22) PCT Filed: Dec. 5, 2019

(86) PCT No.: PCT/JP2019/047719
§ 371 (c)(1),
(2) Date: Jun. 3, 2021

(87) PCT Pub. No.: WO2020/116589
PCT Pub. Date: Jun. 11, 2020

(65) Prior Publication Data
US 2022/0055990 A1  Feb. 24, 2022

(30) Foreign Application Priority Data

Dec. 5, 2018 (JP) .................................. 2018-228589

(51) Int. Cl.
*C07D 211/76* (2006.01)
*B01J 23/44* (2006.01)
(Continued)

(52) U.S. Cl.
CPC ............. *C07D 211/76* (2013.01); *B01J 23/44* (2013.01); *C07C 231/12* (2013.01);
(Continued)

(58) Field of Classification Search
CPC .................................................. C07D 211/76
See application file for complete search history.

(56) References Cited

U.S. PATENT DOCUMENTS

| | | | |
|---|---|---|---|
| 4,859,229 | A | 8/1989 | Wenger et al. |
| 2014/0080914 | A1 | 3/2014 | Kanou et al. |
| 2014/0274688 | A1 | 9/2014 | Fischer et al. |

FOREIGN PATENT DOCUMENTS

| | | |
|---|---|---|
| CN | 105669583 | 6/2016 |
| EP | 2 468 778 | 6/2012 |

(Continued)

OTHER PUBLICATIONS

Extended European Search Report issued Oct. 11, 2022 in corresponding European Patent Application No. 19893405.1.
(Continued)

*Primary Examiner* — Andrew D Kosar
*Assistant Examiner* — Rehana Ismail
(74) *Attorney, Agent, or Firm* — WENDEROTH, LIND & PONACK, L.L.P.

(57) ABSTRACT

An object of this disclosure provides a novel method for producing a fluorovinyl amide compound and the like. The object is achieved by a method for producing a compound represented by formula (1):

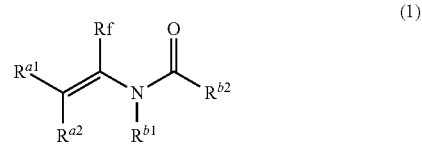

(1)

wherein
Rf is —F or fluoroalkyl,
$R^{a1}$ is —H or an organic group, and
$R^{a2}$ is —H or an organic group, or
(i) $R^{a1}$ and $R^{a2}$, (ii) $R^{a1}$ and Rf, or (iii) Rf and $R^{a2}$, may be linked to each other,
$R^{b1}$ is —H or an organic group, and
$R^{b2}$ is —H or an organic group, or
$R^{b1}$ and $R^{b2}$ may be linked together with their adjacent atoms to form a nitrogen-containing ring optionally having one or more substituents,
the method comprising
step A of reacting a compound represented by formula (2):

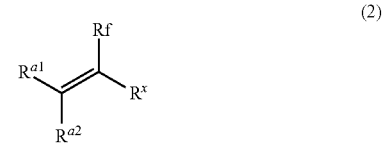

(2)

wherein
$R^x$ is a leaving group,
with a compound represented by formula (3) or a salt thereof:

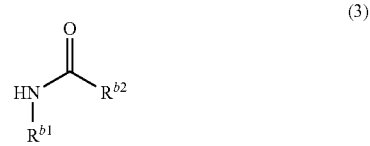

(3)

in the presence of a transition metal catalyst.

18 Claims, No Drawings

(51) Int. Cl.
*C07C 231/12* (2006.01)
*C07D 207/27* (2006.01)
*C07D 209/44* (2006.01)
*C07D 263/22* (2006.01)

(52) U.S. Cl.
CPC ......... *C07D 207/27* (2013.01); *C07D 209/44* (2013.01); *C07D 263/22* (2013.01)

(56) References Cited

FOREIGN PATENT DOCUMENTS

| JP | 63-41466 | 2/1988 | |
|---|---|---|---|
| JP | 11-240859 | 9/1999 | |
| JP | 2007-262159 | 10/2007 | |
| JP | 2016-516712 | 6/2016 | |
| WO | 99/33790 | 7/1999 | |
| WO | 2010/055887 | 5/2010 | |
| WO | WO-2010055887 A1 * | 5/2010 | ........... C07C 303/40 |

OTHER PUBLICATIONS

Jiang et al., "Highly efficient synthesis of chiral α-CF3 amines via Rh-catalyzed asymmetric hydrogenation," Organic Letters, vol. 17, No. 5, 2015, pp. 1154-1156.
Compain et al., "Stereoselective hydrofluorination of ynamides: a straightforward synthesis of novel α-fluoroenamides," Chemical Communications, vol. 48, No. 42, 2012, pp. 5196-5198.
English translation of International Preliminary Report on Patentability and Written Opinion issued Jun. 8, 2021 in International (PCT) Application No. PCT/JP2019/047719.
International Search Report issued Feb. 4, 2020 in International (PCT) Application No. PCT/JP2019/047719.
Wu et al., Royal Society of Chemistry, 2018, vol. 8, pp. 16019-16023.
Gao et al., Tetrahedron Letters, 2015, vol. 56, pp. 4180-4183.
Welchinska et al., Sovremennye Problemy toksikologii, 2013, vol. 1-2, pp. 72-75, English abstract, cited in ISR.
Welchinska et al., Farmatsevtychnyi Zhurnal, 2010, vol. 14, pp. 87-91, English abstract, cited in ISR.
Wojtowiez-Rajchel et al., New Journal of Chemistry, 2010, vol. 34, No. 5, pp. 894-902.
Wojtowiez-Rajchel et al., European Journal of Organic Chemistry, 2008, pp. 368-376.
Kantlehner et al., Science of Synthesis, 2006, Cat. 3, vol. 24, pp. 337-440.
Schantl et al., Science of Synthesis, 2006, Cat. 3, vol. 24, pp. 223-284.
Yu et al., Russian Chemical Bulletin, 1998, vol. 47, No. 12, pp. 2479-2480.
Furin et al., Zhurnal Prikladnoi Khimii, 1996, vol. 69, No. 1, pp. 103-111, cited in ISR.
Snegirev et al., Izvestiya Akademii Nauk, Seriya Khimicheskaya, 1994, vol. 6, pp. 1073-1077, English abstract, cited in ISR.
Inoue et al., Chemistry Express, 1986, vol. 1, No. 9, pp. 531-534, English abstract, cited in ISR.
Del'tsova et al., Seriya Khimicheskaya, 1985, vol. 11, pp. 2533-2537, cited in ISR.
Yanagida et al., The Chemical Society of Japan, 1981, vol. 54, pp. 1151-1158.
Chen et al., Chinese Journal of Chemistry, 2013, vol. 31, pp. 901-907.
Xi et al., Organic and Biomolecular Chemistry, 2017, 15, pp. 7218-7226.
CAS 1952245-92-9, Jul. 14, 2016, pp. 1-7.
Fu-min Liao et al., "Highly Stereoselective Gold-Catalyzed Coupling of Diazo Reagents and Fluorinated Enol Silyl Ethers to Tetrasubstituted Alkenes," Angewandte Chemie International Edition, Jan. 18, 2017, vol. 56, No. 9, pp. 2459-2463.
Fu-min Liao et al., "Recent Advances in the Highly Stereoselective Synthesis of Tri- or Tetra-substitued Monofluoroalkenes," Chinese Journal of Organic Chemistry, Jul. 7, 2017, vol. 37, No. 9, pp. 2175-2186 (with English Abstract).
Mario Pagliaro et al., "New fluorinated functional materials," Journal of Materials Chemistry, Aug. 11, 2005, vol. 15, No. 47, pp. 4981-4991.
Biswajit Ray et al., "Highly Controlled Synthesis of Poly(N-vinylpyrrolidone) and Its Block Copolymers by Organostibine-Mediated Living Radical Polymerization," Macromolecules, Jul. 13, 2006, vol. 39, No. 16, pp. 5259-5265.
Avnish Kumar Mishra et al., "Synthesis of Well-Defined Amphihillic Poly(ε-caprolactone)-b-poly(N-vinylpyrrolidone) Block Copolymers via the Combination of ROP and Xanthate-Mediated RAFT Polymerization," Macromolecules, Mar. 30, 2011, vol. 44, pp. 2465-2473.
Mirela Teodorescu et al., "Poly(vinylpyrrolidone)—A Verasatile Polymer for Biomedical and Beyond Medical Applications," Polymer-Plastics Technology and Engineering, Jun. 2, 2015, vol. 54, No. 9, pp. 923-943.

* cited by examiner

METHOD FOR PRODUCING FLUOROVINYL AMIDE COMPOUND

TECHNICAL FIELD

The present disclosure relates to a method for producing a fluorovinyl amide compound.

BACKGROUND ART

Conventionally known methods for producing a fluorovinyl amide compound include those disclosed, for example, in Non-patent Literature (NPL) 1 and NPL 2. However, both of these methods must use a compound with two aromatic rings as a substrate, and the resulting compound is also limited to a compound with two aromatic rings.

CITATION LIST

Non-patent Literature

NPL 1: Gao et al., Tetrahedron Letters, Volume 56, Issue 28, pages 4180-4183 (2015)
NPL 2: Xi et al., Org. Biomol. Chem., 2017, 15, pages 7218-7226

SUMMARY OF INVENTION

Technical Problem

An object of the present disclosure is to provide, for example, a novel method for producing a fluorovinyl amide compound.

Solution to Problem

The present disclosure encompasses the following embodiments.

Item 1.

A method for producing a compound represented by formula (1):

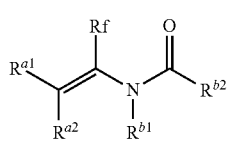

(1)

wherein
Rf is -F or fluoroalkyl,
$R^{a1}$ is -H or an organic group, and
$R^{a2}$ is -H or an organic group, or
(i) $R^{a1}$ and $R^{a2}$, (ii) $R^{a1}$ and Rf, or (iii) Rf and $R^{a2}$, may be linked to each other,
$R^{b1}$ is -H or an organic group, and
$R^{b2}$ is -H or an organic group, or
$R^{b1}$ and $R^{b2}$ may be linked together with their adjacent atoms to form a nitrogen-containing ring optionally substituted with one or more substituents, the method comprising
step A of reacting a compound represented by formula (2):

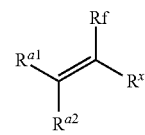

(2)

wherein
$R^x$ is a leaving group, and other symbols are as defined above,
with
a compound represented by formula (3) or a salt thereof:

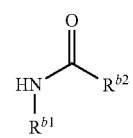

(3)

wherein the symbols in the formula are as defined above, in the presence of a transition metal catalyst.

Item 2.

The production method according to Item 1, wherein Rf is -F or perfluoroalkyl.

Item 3.

The production method according to Item 1 or 2, wherein $R^{a1}$ is -H, an alkyl group optionally substituted with one or more substituents, or an aromatic ring group optionally substituted with one or more substituents.

Item 4.

The production method according to any one of Items 1 to 3, wherein $R^{a2}$ is -H, an alkyl group optionally substituted with one or more substituents, or an aromatic ring group optionally substituted with one or more substituents.

Item 5.

The production method according to any one of Items 1 to 4, wherein either $R^{a1}$ or $R^{a2}$ is -H, and the other is -H or an aromatic ring group optionally substituted with one or more substituents.

Item 6.

The production method according to any one of Items 1 to 5, wherein $R^x$ is a halo group or a sulfonic acid ester group.

Item 7.

The production method according to any one of Items 1 to 6,
wherein
$R^{b1}$ is $-L^b-R^h$,
wherein
$R^h$ is
an aliphatic hydrocarbyl group optionally substituted with one or more substituents, wherein one or more heteroatoms selected from the group consisting of O, S, and Si may be inserted into the aliphatic hydrocarbyl group, or
an aromatic ring group optionally substituted with one or more substituents, and
$L^b$ is a single bond, $-NR^r-$, $-O-$, or $-S-$, wherein $R^r$ is -H or an alkyl group.

Item 8.

The production method according to any one of Items 1 to 7,
wherein
$R^{b2}$ is $-L^b-R^h$,
wherein
$R^h$ is
an aliphatic hydrocarbyl group optionally substituted with one or more substituents, wherein one or more heteroatoms selected from the group consisting of O, S, and Si may be inserted into the aliphatic hydrocarbyl group, or
an aromatic ring group optionally substituted with one or more substituents, and
$L^b$ is a single bond,-$NR^r$-,-O-, or -S-, wherein $R^r$ is -H or an alkyl group.

Item 9.

The production method according to Item 8, wherein $R^{b1}$ and $R^{b2}$ are linked together with their adjacent atoms to form a nitrogen-containing heterocyclic ring optionally substituted with one or more substituents.

Item 10.

The production method according to any one of Items 1 to 9, wherein the transition metal catalyst is at least one member selected from the group consisting of palladium catalysts, copper catalysts, nickel catalysts, platinum catalysts, and iron catalysts.

Item 11.

The production method according to Item 10, wherein the transition metal catalyst is at least one member selected from the group consisting of palladium catalysts, copper catalysts, and nickel catalysts.

Item 12.

The production method according to Item 11, wherein the transition metal catalyst is a palladium catalyst.

Item 13.

The production method according to any one of Items 1 to 12, wherein the reaction of step A is performed in the presence of a coordination compound.

Item 14.

The production method according to Item 13, 5 wherein the coordination compound is a biphenyl compound represented by formula (4-1):

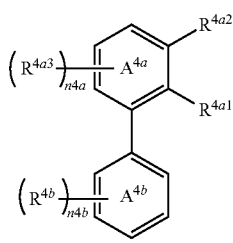

(4-1)

wherein
$A^{4a}$ is a benzene ring,
$A^{4b}$ is a benzene ring,
$R^{4a1}$ is a phosphino group substituted with two $C_{1-20}$ hydrocarbyl groups,
$R^{4a2}$ is an alkyl group or an alkoxy group,
$R^{4a3}$, in each occurrence, is the same or different and represents a substituent,
$R^{4b}$, in each occurrence, is the same or different and represents a substituent,
n4a is a number of 0 to 3, and
n4b is a number of 0 to 5.

Item 15.

The production method according to Item 14, wherein $R^{4a1}$ is a phosphino group substituted with two substituents selected from the group consisting of cyclohexyl, tert-butyl, and adamantyl groups, and
$R^{4a2}$ is a methyl group or a methoxy group.

Item 16.

The production method according to any one of Items 1 to 15, wherein the reaction of step A is performed in the presence of a base.

Item 17.

The production method according to Item 16, wherein the base has a pKa of 36 to 3.6.

Item 18.

The production method according to Item 16, wherein the base is at least one member selected from the group consisting of
(1) acetates, carbonates, hydrogen carbonates, phosphates, hydrogen phosphates, alkoxide salts, hydroxide salts, hydride salts, ammonium salts, or amide salts of alkaline or alkaline earth metals,
(2) polymer-supported bases,
(3) alkali metals, and
(4) amines.

Item 19.

A compound represented by formula (1):

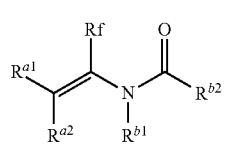

(1)

wherein
Rf is -F or fluoroalkyl,
$R^{a1}$ is-H or an organic group,
$R^{a2}$ is -H or an organic group, or
(i) $R^{a1}$ and $R^{a2}$, (ii) $R^{a1}$ and Rf, or (iii) Rf and $R^{a2}$, may be linked to each other,
$R^{b1}$ is -H or an organic group, and
$R^{b2}$ is -H or an organic group, or
$R^{b1}$ and $R^{b2}$ may be linked together with their adjacent atoms to form a nitrogen-containing ring optionally substituted with one or more substituents, with the proviso that substituted benzimidazole is excluded,
with the proviso that when $R^{a1}$ or $R^{a2}$, or both, are hydrogen, $R^{b2}$ is not a mono-or di-substituted amino group.

Item 20.

The compound according to Item 19, wherein
$R^{a1}$ is -H,
$R^{a2}$ is -H,
$R^{b1}$ is-$L^b$-$R^h$,
$R^{b2}$ is-$L^b$-$R^h$,
wherein
$R^h$, in each occurrence, independently represents an aliphatic hydrocarbyl group optionally substituted with one or more substituents, wherein one or more heteroatoms selected from the group consisting of O, S, and Si may be inserted into the aliphatic hydrocarbyl group, or
an aromatic ring group optionally substituted with one or more substituents, and
$L^b$ is a single bond,-O-, or -S-.

Item 21.

The compound according to Item 20, wherein either $R^{a1}$ or $R^{a2}$ is -H, and the other is -H or an aromatic ring group optionally substituted with one or more substituents.

Item 22.

The compound according to Item 21, wherein $R^{a1}$ and $R^{a2}$ each independently represent an organic group.

Item 23.

The compound according to any one of Items 19 to 22, wherein $R^{b1}$ and $R^{b2}$ are linked together with their adjacent atoms to form a nitrogen-containing heterocyclic ring optionally substituted with one or more substituents.

Advantageous Effects of Invention

The present disclosure provides, for example, a novel method for synthesizing a fluorovinyl amide compound from a fluorine-containing vinyl compound.

DESCRIPTION OF EMBODIMENTS

Terms

The symbols and abbreviations in the present specification can be understood as indicating the meanings typically used in the technical field to which the present disclosure pertains in accordance with the context of the specification, unless otherwise specified.

In the present specification, the terms "comprise" and "contain" are used with the intention of including the meaning of the phrases "consist essentially of" and "consist of."

Unless otherwise specified, the steps, treatments, or operations described in the present specification may be performed at room temperature.

In the present specification, room temperature can refer to a temperature in the range of 10 to 40° C.

In the present specification, the term "$C_{n-m}$" (wherein n and m each represent a number) indicates that the number of carbon atoms is n or more and m or less, as a person skilled in the art would usually understand.

For the sake of confirmation, the description of each substituent may also apply to the description of substituents that partially contain the substituent. More specifically, for example, the description of an alkyl group may also apply to the alkyl moiety in an aralkyl group.

In the present specification, unless otherwise specified, examples of "halogen atom" include fluorine, chlorine, iodine, and bromine.

In the present specification, unless otherwise specified, the term "halogeno group" or "halo group" includes fluoro, chloro, bromo, and iodo.

As a person skilled in the art would usually understand, the suffix "fluoro" means that one or more hydrogen atoms are replaced by a fluoro group.

As a person skilled in the art would usually understand, the suffix "perfluoro" means that all hydrogen atoms are replaced by a fluoro group.

In the present specification, unless otherwise specified, the term "organic group" refers to a group formed by removing one hydrogen atom from an organic compound. As can be understood from this, an organic group contains one or more carbon atoms.

In the present specification, unless otherwise specified, the term "organic group" includes
(1) hydrocarbon groups and
(2) hydrocarbon groups having one or more heteroatoms (e.g., nitrogen, oxygen, sulfur, phosphorus, halogen).

In the present specification, unless otherwise specified, the term "hydrocarbon group" refers to a group consisting only of carbon and hydrogen.

A hydrocarbon group can also be referred to as hydrocarbyl (group).

In the present specification, unless otherwise specified, examples of "hydrocarbyl" include
(1) aliphatic hydrocarbyl groups (e.g., benzyl group) optionally substituted with one or more aromatic hydrocarbyl groups, and
(2) aromatic hydrocarbyl groups optionally substituted with one or more aliphatic hydrocarbyl groups.

An aromatic hydrocarbon group can also be referred to as aryl (group).

In the present specification, unless otherwise specified, the "hydrocarbyl" can have a linear, branched, or cyclic structure, or a combination thereof.

In the present specification, unless otherwise specified, the "aliphatic hydrocarbyl (group)" can be saturated or unsaturated.

In the present specification, unless otherwise specified, examples of the "aliphatic hydrocarbyl (groups)" include alkyl, alkenyl, alkynyl, and cycloalkyl. In the present specification, the term "(cyclo)alkyl" refers to alkyl or cycloalkyl, as a person skilled in the art would usually understand.

In the present specification, unless otherwise specified, "alkyl (group)" may have a linear or branched structure, or a combination thereof.

In the present specification, unless otherwise specified, examples of "alkyl (group)" include $C_{1-11}$ linear or branched alkyl (groups). Specific examples include methyl, ethyl, propyl (e.g., n-propyl, isopropyl), butyl (e.g., n-butyl, isobutyl, sec-butyl, tert-butyl), pentyl (e.g., n-pentyl, tert-pentyl, neopentyl, isopentyl, sec-pentyl, 3-pentyl), hexyl, heptyl, octyl, nonyl, and decyl.

In the present specification, unless otherwise specified, examples of "alkenyl (group)" include $C_{1-10}$ linear or branched alkenyl groups. Specific examples include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the present specification, unless otherwise specified, examples of "alkynyl (group)" include linear or branched alkynyl groups having 2 to 6 carbon atoms. Specific examples include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the present specification, unless otherwise specified, examples of "cycloalkyl (group)" include cycloalkyl groups having 3 to 10 carbon atoms. Specific examples include cyclopropyl, cyclobutyl, cyclopentyl, cyclohexyl, cycloheptyl, cyclooctyl, and adamantyl.

In the present specification, unless otherwise specified, examples of "aromatic hydrocarbon group (or aryl))" include $C_{6-14}$ aromatic hydrocarbon groups (or aryl). Specific examples include phenyl, naphthyl, phenanthryl, anthryl, and pyrenyl.

In the present specification, unless otherwise specified, examples of "aromatic hydrocarbon ring" include $C_{6-14}$ aromatic hydrocarbon rings. Specific examples includes a benzene ring, a naphthalene ring, an anthracene ring, and a phenanthrene ring.

In the present specification, unless otherwise specified, the term "alkoxy (group)" may refer to a group represented by RO— (wherein R is alkyl (e.g., $C_{1-11}$ alkyl)). Examples include $C_{1-11}$ alkoxy groups (e.g., methoxy, ethoxy, propoxy, isopropoxy, n-butoxy, isobutoxy, sec-butoxy, pentyloxy, and hexyloxy).

In the present specification, unless otherwise specified, the term "alkylcarbonyloxy (group)" may refer to a group represented by RCO—O— (wherein R is an alkyl group).

Specific examples include acetoxy.

In the present specification, unless otherwise specified, the term "ester group" refers to an organic group having at least one ester bond (i.e., —C(=O)—O— or —O—C(=O)—).

Examples of the "ester group" include
(1) groups represented by the formula: $RCO_2$— (wherein R is an alkyl group), and
(2) groups represented by the formula: $R^a$—$CO_2$—$R^b$— (wherein $R^a$ is an alkyl group, and $R^b$ is an alkylene group).

In the present specification, unless otherwise specified, the term "ether group" refers to a group having one or more ether bonds (—O—).

Examples of the "ether group" include polyether groups.

Examples of polyether groups include groups represented by the formula: $R^a$—$(O—R^b)_n$— (wherein $R^a$ is an alkyl group, $R^b$, in each occurrence, is the same or different and represents an alkylene group, and n is an integer of 1 or more).

An alkylene group refers to a divalent group formed by removing one hydrogen atom from the alkyl group mentioned above.

Examples of the "ether group" also include hydrocarbyl ether groups.

The term "hydrocarbyl ether (group)" refers to hydrocarbyl (group) having one or more ether bonds.

The "hydrocarbyl (group) having one or more ether bonds" may be a hydrocarbyl group having one or more ether bonds internally or at the end of the group.

Examples include alkoxy and benzyloxy.

Examples of the "hydrocarbyl having one or more ether bonds" include alkyl having one or more ether bonds.

The "alkyl having one or more ether bonds" may be an alkyl group into which one or more ether bonds are inserted.

Such a group may also be referred to as an alkyl ether group.

In the present specification, unless otherwise specified, the term "acyl (group)" includes alkanoyl.

In the present specification, unless otherwise specified, the "alkanoyl (group)" refers to, for example, a group represented by RCO— (wherein R is an alkyl group).

Specific examples include acetyl.

In the present specification, unless otherwise specified, the term "cyclic group" includes cyclic aliphatic hydrocarbon groups (e.g., cycloalkyl), aromatic hydrocarbon groups (aryl), and heterocyclic groups.

In the present specification, unless otherwise specified, the term "heterocyclic group" includes non-aromatic heterocyclic groups and heteroaryl groups.

In the present specification, examples of "heterocyclic group" include 5- to 18-membered, 5- to 16-membered, 5- to 12-membered, 5- to 11-membered, 11- to 18-membered, 12- to 18-membered, 11- to 17-membered, 12- to 17-membered, and 5- to 6-membered heterocyclic groups.

In the present specification, unless otherwise specified, a "heterocyclic group" may be monocyclic, bicyclic, tricyclic, or tetracyclic.

In the present specification, unless otherwise specified, the "heterocyclic group" may be, for example, a heterocyclic group containing, in addition to carbon, 1 to 4 heteroatoms selected from oxygen, sulfur, and nitrogen as ring-constituting atoms.

In the present specification, unless otherwise specified, the "non-aromatic heterocyclic group" may be saturated or unsaturated.

In the present specification, unless otherwise specified, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, and dihydroquinolyl.

In the present specification, unless otherwise specified, examples of "heteroaryl (group)" include monocyclic aromatic heterocyclic groups (e.g., 5- or 6-membered monocyclic aromatic heterocyclic groups), and aromatic fused heterocyclic groups (e.g., 5- to 18-membered aromatic fused heterocyclic groups).

In the present specification, unless otherwise specified, examples of "5- or 6-membered monocyclic aromatic heterocyclic group" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), and pyrazinyl.

In the present specification, unless otherwise specified, examples of "5- to 18-membered aromatic fused heterocyclic group" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]

thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), and imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl).

In the present specification, examples of "aromatic group" (or "aromatic ring group") include aryl groups and aromatic heterocyclic groups.

1. Production Method

The production method of the present disclosure is a method for producing a compound represented by formula (1):

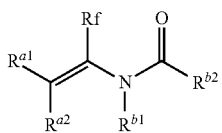

wherein
Rf is —F or fluoroalkyl,
$R^{a1}$ is —H or an organic group, and
$R^{a2}$ is —H or an organic group, or
(i) $R^{a1}$ and $R^{a2}$, (ii) $R^{a1}$ and Rf, or (iii) Rf and $R^{a2}$, may be linked to each other,
$R^{b1}$ is —H or an organic group, and
$R^{b2}$ is —H or an organic group, or
$R^{b1}$ and $R^{b2}$ may be linked together with their adjacent atoms to form a nitrogen-containing ring optionally substituted with one or more substituents, the method comprising step A of reacting a compound represented by formula (2):

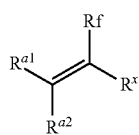

wherein
$R^x$ is a leaving group, and other symbols are as defined above, with
a compound represented by formula (3) or a salt thereof:

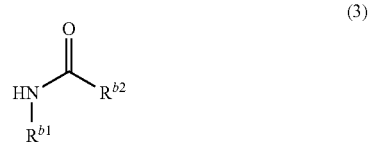

wherein the symbols in the formula are as defined above, in the presence of a transition metal catalyst.

Examples of the salts include salts formed with an acid selected from the group consisting of inorganic acids and organic acids. Examples of salts of inorganic acids include salts with an acid comprising, as its component, a non-metal element except for carbon.

Examples of salts of organic acids include carboxylate, sulfonate, and phosphate.

Specific examples of salts of inorganic acids include hydrochloride, sulfate, sulfite, nitrate, nitrite, hypochlorite, chlorite, chlorate, perchlorate, hydrobromide, and hydroiodide.

Specific examples of salts of organic acids include acetate, trifluoroacetate, para-toluenesulfonate, methanesulfonate, trifluoromethanesulfonate, and dimethylphosphonate.

Particularly preferable examples of the salts include hydrochloride.

Rf is preferably —F or perfluoroalkyl.

Rf is more preferably —F or linear or branched $C_{1-4}$ perfluoroalkyl.

Rf is more preferably —F or linear or branched $C_{1-3}$ perfluoroalkyl.

Rf is even more preferably —F or linear or branched $C_{1-2}$ perfluoroalkyl.

$R^{a1}$ is preferably
(1) -H,
(2) an alkyl group optionally substituted with one or more substituents, or
(3) an aromatic ring group optionally substituted with one or more substituents.

$R^{a1}$ is more preferably
(1) -H,
(2) a linear or branched $C_{1-10}$ alkyl group optionally substituted with one or more substituents selected from the group consisting of alkoxy, aryl, heteroaryl, alkenyl, alkynyl, acyl, ester, and halogeno groups, or
(3) a $C_{6-20}$ aryl group or a 3- to 7-membered heteroaryl group each optionally substituted with one or more substituents selected from the group consisting of alkyl, alkoxy, aryl, alkenyl, alkynyl, acyl, ester, and cyano groups.

$R^{a1}$ is more preferably
(1) -H,
(2) linear or branched $C_{1-5}$ alkyl optionally substituted with one or more substituents selected from the group consisting of alkoxy, aryl, heteroaryl, alkenyl, and alkynyl groups, or (3) C$_{6-15}$ aryl or 4- to 6-membered heteroaryl each optionally substituted with one or more substituents selected from the group consisting of alkyl, alkoxy, aryl, alkenyl, and alkynyl groups.

R$^{a1}$ is even more preferably
(1) -H,
(2) linear or branched C$_{1-4}$ alkyl optionally substituted with one or more substituents selected from the group consisting of alkoxy, aryl, and heteroaryl groups, or
(3) C$_{6-12}$ aryl optionally substituted with one or more substituents selected from the group consisting of alkyl, alkoxy, and aryl groups.

R$^{a1}$ is particularly preferably —H or phenyl.
R$^{a1}$ is most preferably —H.
R$^{a2}$ is preferably
(1) -H,
(2) an alkyl group optionally substituted with one or more substituents, or
(3) an aromatic ring group optionally substituted with one or more substituents.

R$^{a2}$ is more preferably
(1) -H,
(2) linear or branched C$_{1-10}$ alkyl optionally substituted with one or more substituents selected from the group consisting of alkoxy, aryl, heteroaryl, alkenyl, alkynyl, halogeno, acyl, and ester, or
(3) C$_{6-20}$ aryl or 3- to 7-membered heteroaryl each optionally substituted with one or more substituents selected from the group consisting of alkyl, alkoxy, aryl, alkenyl, alkynyl, acyl, cyano, and ester groups.

R$^{a2}$ is more preferably
(1) -H,
(2) linear or branched C$_{1-6}$ alkyl optionally substituted with one or more substituents selected from the group consisting of alkoxy, aryl, heteroaryl, alkenyl, and alkynyl groups, or
(3) C$_{6-15}$ aryl or 4- to 6-membered heteroaryl each optionally substituted with one or more substituents selected from the group consisting of alkyl, alkoxy, aryl, alkenyl, and alkynyl groups.

R$^{a2}$ is even more preferably
(1) -H,
(2) linear or branched C$_{1-4}$ alkyl optionally substituted with one or more substituents selected from the group consisting of alkoxy, aryl, and heteroaryl groups, or
(3) C$_{6-12}$ aryl optionally substituted with one or more substituents selected from the group consisting of alkyl, alkoxy, and aryl groups.

R$^{a2}$ is particularly preferably —H or phenyl.
R$^{a2}$ is most preferably —H.

It is preferred that either R$^{a1}$ or R$^{a2}$ be —H, and the other be —H or an aromatic ring group optionally substituted with one or more substituents.

It is more preferred that
either R$^{a1}$ or R$^{a2}$ be -H, and
the other be
(1) -H,
(2) linear or branched C$_{1-10}$ alkyl optionally substituted with one or more substituents selected from the group consisting of alkoxy, aryl, heteroaryl, alkenyl, alkynyl, ester, halogeno, and acyl groups, or
(3) C$_{6-20}$ aryl or 3- to 7-membered heteroaryl each optionally substituted with one or more substituents selected from the group consisting of alkyl, alkoxy, aryl, alkynyl, alkenyl, cyano, ester, and acyl groups.

It is even more preferred that
either R$^{a1}$ or R$^{a2}$ be -H, and
the other be
(1) -H,
(2) linear or branched C$_{1-6}$ alkyl optionally substituted with one or more substituents selected from the group consisting of alkoxy, aryl, heteroaryl, alkenyl, and alkynyl, or
(3) C$_{6-15}$ aryl or 4- to 6-membered heteroaryl each optionally substituted with one or more substituents selected from the group consisting of alkyl, alkoxy, aryl, alkynyl, and alkenyl groups.

It is still more preferred that
either R$^{a1}$ or R$^{a2}$ be -H, and
the other be
(1) -H,
(2) linear or branched C$_{1-3}$ alkyl optionally substituted with one or more substituents selected from the group consisting of alkoxy, aryl, and heteroaryl groups, or
(3) C$_{6-12}$ aryl optionally substituted with one or more substituents selected from the group consisting of alkyl, alkoxy, and aryl groups.

It is particularly preferred that either R$^{a1}$ or R$^{a2}$ is —H, and the other be —H or phenyl.

R$^{x}$ is preferably a halo group or a sulfonic acid ester group.
R$^{x}$ is more preferably a halo group.
R$^{x}$ is more preferably chloro.

It is preferred that R$^{b1}$ be -L$^{b}$-R$^{h}$,
wherein R$^{h}$ is
an aliphatic hydrocarbyl group optionally substituted with one or more substituents (one or more heteroatoms selected from the group consisting of O, S, and Si may be inserted into the aliphatic hydrocarbyl group), or an aromatic ring group optionally substituted with one or more substituents, and
L$^{b}$ is a single bond, —NR$^{r}$—, —O—, or —S—, wherein R$^{r}$ is —H or an alkyl group.

It is more preferred that R$^{b1}$ be -L$^{b}$-R$^{h}$,
wherein R$^{h}$ is
(1) a C$_{1-10}$ aliphatic hydrocarbyl group optionally substituted with one or more substituents selected from the group consisting of alkoxy, aryl, heteroaryl, alkenyl, alkynyl, cyano, nitro, ester, and halogeno (one or more heteroatoms selected from the group consisting of O, S, and Si may be inserted into the aliphatic hydrocarbyl group), or
(2) a 5- to 7-membered aromatic ring group optionally substituted with one or more substituents selected from the group consisting of alkyl, alkoxy, aryl, heteroaryl, acyl, cyano, ester, nitro, and halogeno groups, and
L$^{b}$ is a single bond,-NR$^{r}$-,-O-, or -S-, wherein R$^{r}$ is-H or a C$_{1-10}$ alkyl group.

It is even more preferred that R$^{b1}$ be -L$^{b}$-R$^{h}$,
wherein R$^{h}$ is
(1) a C$_{1-5}$ aliphatic hydrocarbyl group optionally substituted with one or more substituents selected from the group consisting of alkoxy, aryl, heteroaryl, alkenyl, and alkynyl (one or more heteroatoms selected from the group consisting of O, S, and Si may be inserted into the aliphatic hydrocarbyl group), or
(2) C$_{6-14}$ aryl or 5- to 7-membered heteroaryl each optionally substituted with one or more substituents selected from the group consisting of alkyl, alkoxy, aryl, and heteroaryl groups, and L$^{b}$ is a single bond,-NR$^{r}$-,-O-, or -S-, wherein R$^{r}$ is-H or a C$_{1-5}$ alkyl group.

It is preferred that $R^{b2}$ be -$L^b$-$R^h$,
wherein $R^h$ is
an aliphatic hydrocarbyl group optionally substituted with one or more substituents (one or more heteroatoms selected from the group consisting of O, S, and Si may be inserted into the aliphatic hydrocarbyl group), or
an aromatic ring group optionally substituted with one or more substituents, and
$L^b$ is a single bond, —NR$^r$—, —O—, or —S—.

It is more preferred that $R^{b2}$ be -$L^b$-$R^h$,
wherein $R^h$ is
(1) a $C_{1-10}$ aliphatic hydrocarbyl group optionally substituted with one or more substituents selected from the group consisting of alkoxy, aryl, heteroaryl, alkenyl, alkynyl, cyano, nitro, ester, and halogeno groups (one or more heteroatoms selected from the group consisting of O, S, and Si may be inserted into the aliphatic hydrocarbyl group), or
(2) a 5- to 7-membered aromatic ring group optionally substituted with one or more substituents selected from the group consisting of alkyl, alkoxy, aryl, heteroaryl, acyl, cyano, ester, nitro, and halogeno groups, and
$L^b$ is a single bond,-NRI-,-O-, or -S-, wherein $R^r$ is -H or a $C_{1-10}$ alkyl group.

It is furthermore preferred that $R^{b2}$ be -$L^b$-$R^h$,
wherein $R^h$ is
(1) a $C_{1-5}$ aliphatic hydrocarbyl group optionally substituted with one or more substituents selected from the group consisting of alkoxy, aryl, heteroaryl, alkenyl, and alkynyl (one or more heteroatoms selected from the group consisting of O, S, and Si may be inserted into the aliphatic hydrocarbyl group), or
(2) $C_{6-14}$ aryl or 5- to 6-membered heteroaryl each optionally substituted with one or more substituents selected from the group consisting of alkyl, alkoxy, aryl, and heteroaryl groups, and $L^b$ is a single bond,-NR$^r$-,-O-, or -S-, wherein $R^r$ is -H or a $C_{1-5}$ alkyl group.

Alternatively, $R^{b1}$ and $R^{b2}$ may be linked together with their adjacent atoms to form a nitrogen-containing ring optionally substituted with one or more substituents.

The structure of the nitrogen-containing ring may be understood from the structure of $R^{b1}$ and $R^{b2}$ described above.

The linkage between $R^{b1}$ and $R^{b2}$ may be formed between the end of $R^{b1}$ and the end of $R^{b2}$, between the end of $R^{b1}$ and the interior of $R^{b2}$, or between the end of $R^{b1}$ and the interior of $R^{b2}$.

The linkage may occur at one or more moieties. That is, the ring can be, for example, monocyclic, bicyclic, or tricyclic.

The ring may be, for example, a monocyclic or bicyclic, 5- to 10-membered nitrogen-containing heterocyclic ring optionally further substituted with one or more substituents, in addition to the oxo group shown in formula (1).

The "monocyclic or bicyclic, 5- to 10-membered nitrogen-containing heterocyclic ring" may contain one or more heteroatoms (e.g., nitrogen, oxygen, sulfur) in addition to one nitrogen atom as shown in Formula (1).

Specific examples thereof include pyrrole, pyrazole, 1,3-oxazole, isoxazole, 1,3-thiazole, isothiazole, pyrrolidine, pyrazolidine, imidazolidine, pyridine, pyridazine, pyrimidine, 1,2-oxazine, 1,4-oxazine, 1,2-thiazine, 1,4-thiazine, piperidine, piperazine, and morpholine.

Examples of substituents that may be present in the "monocyclic or bicyclic, 5- to 10-membered nitrogen-containing heterocyclic ring" include alkyl, alkoxy, alkenyl, alkynyl, acyl, ester, cyano, amino, and formyl groups.

Transition Metal Catalyst

Preferable examples of transition metals in transition metal catalysts for use in step A above include palladium, copper, silver, gold, nickel, platinum, cobalt, rhodium, iridium, iron, ruthenium, manganese, chromium, and zirconium.

Specifically, preferable examples of the transition metal catalyst include palladium catalysts, copper catalysts, silver catalysts, gold catalysts, nickel catalysts, platinum catalysts, cobalt catalysts, rhodium catalysts, iridium catalysts, iron catalysts, ruthenium catalysts, manganese catalysts, chromium catalysts, and zirconium catalysts.

The transition metal catalyst is more preferably one or more member selected from the group consisting of palladium catalysts, copper catalysts, and nickel catalysts.

Examples of the palladium catalysts include
(1) zerovalent palladium complexes;
(2) zerovalent palladium complexes generated from monovalent or divalent palladium complexes during a reaction; and
(3) complexes obtained by mixing these palladium complexes with at least one compound (ligand) selected from the group consisting of ketones, diketones, phosphines, diamines, bipyridines, and phenanthrolines.

In the present specification, specific examples of zerovalent palladium complexes include $Pd_2(dba)_3$ (dba is dibenzylideneacetone), $Pd_2(dba)_3$-$CHCl_3$, $Pd(dba)_2$, $Pd(cod)_2$ (cod is cycloocta-1,5-diene), $Pd(dppe)_2$ (dppe is 1,2-bis(diphenylphosphino)ethane), $Pd(PCy_3)_2$ (Cy is cyclohexyl), $Pd(Pt-Bu_3)_2$ (t-Bu is t-butyl), $Pd(PPh_3)_4$ (Ph is phenyl), and tris{tris[3,5-bis(trifluoromethyl)phenyl]phosphine}palladium (0).

In the present specification, examples of monovalent palladium complexes include palladium complexes represented by the following chemical formula:

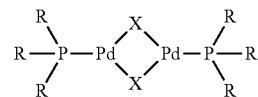

wherein
X is a chlorine atom, a bromine atom, or an iodine atom, and
R, in each occurrence, is the same or different and represents a $C_{1-20}$ alkyl group, a $C_{2-20}$ alkenyl group, a $C_{2-20}$ alkynyl group, or an aryl group.

Of these, preferable specific examples include di-μ-chlorobis (tri-tert-butylphosphine)dipalladium (I), di-μ-bromobis (tri-tert-butylphosphine)dipalladium (I), di-μ-iodobis (tri-tert-butylphosphine)dipalladium (I), di-μ-chlorobis {tri (1-adamantyl)phosphine}dipalladium (I), di-μ-bromobis {tri (1-adamantyl)phosphine}dipalladium (I), and di-μ-iodobis{tri(1-adamantyl)phosphine}dipalladium (I).

In the present specification, specific examples of divalent palladium complexes include
(1) palladium chloride, palladium bromide, palladium acetate, bis (acetylacetonato)palladium (II), dichloro ($\eta^4$-1, 5-cyclooctadiene) palladium (II), dibromo ($\eta^4$-1,5-cyclooctadiene) palladium (II), bis(acetonitrile)dichloropalladium (II), bis (benzonitrile)dichloropalladium (II), and di-μ-chlorobis{($\eta$-allyl)palladium} (II); and
(2) complexes obtained by binding a phosphine ligand, such as triphenylphosphine, to these complexes.

These divalent palladium complexes are, for example, reduced by a reducing species (e.g., phosphines, reducing agents, and organic metal reagents) that is co-present during a reaction, thereby generating zerovalent palladium complexes.

The above zerovalent palladium complexes or zerovalent palladium complexes generated from monovalent or divalent palladium complexes through reduction can interact with a compound (ligand), such as ketones, diketones, phosphines, diamines, bipyridines, and phenanthrolines optionally added during a reaction, and can be converted into zerovalent palladium complexes that are involved in the reaction.

It is not always clarified how many ligands are bound to a zerovalent palladium complex during the reaction.

Examples of the nickel catalysts include zerovalent nickel complexes; zerovalent nickel complexes generated during a reaction from divalent nickel complexes; and complexes obtained by mixing these nickel complexes with at least one compound (ligand) selected from the group consisting of ketones, diketones, phosphines, diamines, bipyridines, and phenanthrolines.

Examples of zerovalent nickel complexes include Ni(cod)$_2$, Ni(cdd)$_2$ (cdd is cyclodeca-1,5-diene), Ni(cdt)$_2$ (cdt is cyclodeca-1,5,9-triene), Ni(vch)$_2$ (vch is 4-vinylcyclohexene), Ni(CO)$_4$, (PCy$_3$)$_2$Ni—N≡N—Ni(PCy$_3$)$_2$, and Ni(PPh$_3$)$_4$.

Examples of divalent nickel complexes include nickel chloride, nickel bromide, nickel acetate, bis(acetylacetonato)nickel(II), nickel(II) trifluoromethanesulfonate, complexes obtained by binding a phosphine ligand, such as triphenylphosphine, to these complexes, and nickel carbene complexes.

These divalent nickel complexes are, for example, reduced by a reducing species (e.g., phosphines, zinc, and organic metal reagents) that is co-present during a reaction, thereby generating zerovalent nickel complexes.

The zerovalent nickel complexes generated from the zerovalent nickel complexes or divalent nickel complexes through reduction can interact with a ligand that is optionally added during a reaction, and can be converted to zerovalent nickel complexes that are involved in the reaction. The number of ligands coordinated to a zerovalent nickel complex during the reaction is not always clear.

Examples of the copper catalysts include copper salts and copper complexes (copper complex salts).

Examples include halogen salts, carboxylic acid (e.g., acetic acid) salts, acetylacetone complexes, alkoxide salts (e.g., phenol salts), carbonates, hydrogen carbonates, sulfonates (e.g., copper sulfate), nitrates (e.g., copper nitrate), cyanides, copper oxides, copper hydroxides, thiosulfate complexes, copper phosphate, copper thiophenecarboxylate, and 1,10-phenanthroline copper complexes.

The transition metal catalyst is particularly preferably a palladium catalyst.

Using the ligands mentioned above, the complexes mentioned above as the transition metal catalysts are usually formed into a homogeneous solution with a reaction substrate and used in a reaction. Alternatively, these complexes can also be used as a heterogeneous catalyst dispersed in or supported on a polymer, such as polystyrene or polyethylene.

Such heterogeneous catalysts have an advantage in processes such as a catalyst recovering process.

Specific examples of catalyst structures thereof include, but are not limited to, those in which a metal atom (palladium in the example shown in the following chemical formula) is immobilized by, for example, a polymeric phosphine in which phosphine units are introduced into a cross-linked polystyrene (PS) polymer chain, as shown in the following chemical formula.

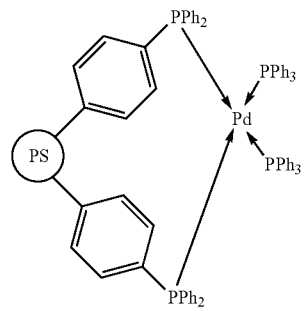

The transition metal catalyst used in step A described above may be supported on a carrier.

Such a supported catalyst has a cost advantage because the catalyst can be recycled.

Examples of the carriers include carbon, alumina, silica gel-alumina, silica gel, barium carbonate, barium sulfate, calcium carbonate, titanium oxide, zirconium oxide, calcium fluoride, and zeolite.

In addition, the polymeric phosphines disclosed in the following documents can also be used.
1) Kanbara et al., Macromolecules, 2000, vol. 33, p. 657
2) Yamamoto et al., J. Polym. Sci., 2002, vol. 40, p. 2637
3) JPH06-032763A
4) JP2005-281454A
5) JP2009-527352A Examples of ketones as the ligand include dibenzylideneacetone.

Examples of diketones as the ligand include (3-diketones, such as acetylacetone, 1-phenyl-1,3-butanedione, 1,3-diphenylpropanedione, and hexafluoroacetylacetone.

Preferable examples of phosphines as the ligand include di(cyclo)alkylmonoaryl phosphines, diarylmono(cyclo)alkyl phosphines, tri(cyclo)alkyl phosphines, triaryl phosphines, and bidentate diphosphines.

Specific examples of di(cyclo)alkylmonoaryl phosphines include diisopropylphenyl phosphine, diisopropyl(o-tolyl) phosphine, diisopropyl(2,6-dimethylphenyl)phosphine, diisopropyl pentafluorophenyl phosphine, di-n-butylphenyl phosphine, di-n-butyl(o-tolyl)phosphine, di-n-butyl(2,6-dimethylphenyl)phosphine, di-n-butyl pentafluorophenyl phosphine, di-tert-butylphenyl phosphine, di-tert-butyl(o-tolyl)phosphine, di-tert-butyl(2,6-dimethylphenyl)phosphine, di-tert-butyl pentafluorophenyl phosphine, dicyclohexylphenyl phosphine, dicyclohexyl(o-tolyl)phosphine, dicyclohexyl(2,6-dimethylphenyl)phosphine, dicyclohexyl pentafluorophenyl phosphine, di(l-adamantyl)phenylphosphine, di(1-adamantyl)(o-tolyl) phosphine, di(1-adamantyl)(2,6-dimethylphenyl)phosphine, di(l-adamantyl)pentafluorophenyl phosphine, 2-dicyclohexylphosphino-2',6'-diisopropoxybiphenyl, 2-dicyclohexylphosphino-2',6'-dimethoxybiphenyl, 2-dicyclohexylphosphino-2',4',6'-triisopropylbiphenyl, 2-dicyclohexylphosphino-2'-(N,N-dimethylamino)biphenyl, 2-(dicyclohexylphosphino)-3,6-dimethoxy-2',4',6'-triisopropyl-1,1'-biphenyl, 2'-dicyclohexylphosphino-2,4,6-trimethoxybiphenyl, 2-dicyclohexylphosphino-2'-methylbiphenyl, 2-di-tert-butylphosphino-2'-methylbiphenyl, 2-di-tert-butylphosphino-2'-(N,N-dimethylamino)biphenyl, 2-di-tert-butylphosphino-3,4,5,6-tetramethyl-2',4',6'-triisopropyl-1, 1'-biphenyl, 2-(di-tert-butylphosphino)-2',4',6'-triisopropyl-3,6-dimethoxy-1,1'-biphenyl, 2-di-tert-butylphosphino-2',4',6'-triisopropylbiphenyl, (2-biphenyl)dicyclohexylphosphine, (2-biphenyl)di-tert-butylphosphine, (3R,5R)-adamantan-1-yl(3S,5-adamantan-1-yl)(2',4',6'-triisopropyl-3,6-dimethoxy-(1,1'-biphenyl)-2-yl)phosphine, and 2-(di-tert-butylphosphino)-3-methoxy-6-methyl-2',4',6'-triisopropyl-1,1'-biphenyl.

Specific examples of diarylmono(cyclo)alkyl phosphines include diphenylmethylphosphine, diphenylisopropylphosphine, n-butyl diphenylphosphine, tert-butyl diphenylphosphine, cyclohexyl diphenylphosphine, (1-adamantyl)diphenylphosphine, di(o-tolyl)methylphosphine, di(o-tolyl)isopropylphosphine, n-butyldi(o-tolyl)phosphine, tert-butyldi(o-tolyl)phosphine, cyclohexyldi(o-tolyl)phosphine, (1-adamantyl)di(o-tolyl)phosphine, bis(2,6-dimethylphenyl)methylphosphine, bis(2,6-dimethylphenyl)isopropylphosphine, bis(2,6-dimethylphenyl)-n-butylphosphine, bis(2,6-dimethylphenyl)-tert-butylphosphine, bis(2,6-dimethylphenyl)cyclohexylphosphine, (1-adamantyl)bis(2,6-dimethylphenyl)phosphine, bis(pentafluorophenyl)methylphosphine, bis(pentafluorophenyl)isopropylphosphine, bis(pentafluorophenyl)-n-butylphosphine, bis(pentafluorophenyl)-tert-butylphosphine, bis(pentafluorophenyl)cyclohexylphosphine, and (1-adamantyl)bis(pentafluorophenyl)phosphine.

Specific examples of tri(cyclo)alkyl phosphines include tri ($C_{3-20}$ (cyclo)alkyl)phosphines, such as tricyclohexylphosphine, triisopropylphosphine, tri-tert-butylphosphine, trihexylphosphine, tri(1-adamantyl)phosphine, tricyclopentylphosphine, di-tert-butyl methylphosphine, cyclohexyldi-tert-butylphosphine, di-tert-butyl neopentylphosphine, di-tert-butyl isopropylphosphine, di-tert-butyl (2-butenyl) phosphine, di-tert-butyl(3-methyl-2-butenyl)phosphine, 1-adamantyl-di-tert-butylphosphine, tert-butyldi(1-adamantyl)phosphine, di(1-adamantyl)isopropylphosphine, cyclohexyldi(1-adamantyl)phosphine, n-butyldi(l-adamantyl)phosphine, tribicyclo[2,2,2]octylphosphine, and trinorbornyl phosphine.

Specific examples of triaryl phosphines include tri(monocyclic aryl)phosphines, such as triphenylphosphine, trimesitylphosphine, tri(o-tolyl)phosphine, tris{(4-trifluoromethyl)phenyl}phosphine, tris(pentafluorophenyl)phosphine, and tris[3,5-bis(trifluoromethyl)phenyl]phosphine.

Specific examples of bidentate diphosphines include 1,2-bis(diphenylphosphino)ethane, 1,3-bis(diphenylphosphino)propane, 1,4-bis(diphenylphosphino)butane, 1,5-bis(diphenylphosphino)pentane, 1,3-bis(diisopropylphosphino)propane, 1,4-bis(diisopropylphosphino)butane, 1,3-bis(dicyclohexylphosphino)propane, 1,4-bis(dicyclohexylphosphino)butane, bis(diphenylphosphinophenyl)ether, bis(dicyclohexylphosphinophenyl)ether, 1,1'-bis(diphenylphosphino)ferrocene, 1,1'-bis(dicyclohexylphosphino)ferrocene, 1,1'-bis(diisopropylphosphino)ferrocene, 1,1'-bis(di-tert-butylphosphino)ferrocene, 1,2-bis(di-tert-butylphosphinomethyl)benzene, 4,6-bis(diphenylphosphino)phenoxazine, 4,5-bis(diphenylphosphino)-9,9'-dimethylxanthene, 4,5-bis(di-tert-butylphosphino)-9,9'-dimethylxanthene, and 2,2'-bis(diphenylphosphino)-1,1'-binaphthyl.

The transition metal catalysts may be used alone, or in a combination of two or more.

The phosphines may be tetrafluoro borates (e.g., tri(cyclo)alkylphosphonium tetrafluoroborates, such as trihexylphosphonium tetrafluoroborate and tri-tert-butyl phosphonium tetrafluoroborate).

Such a salt can be reacted with a base described in detail below to give a free body of phosphine (e.g., tri(cyclo)alkylphosphine, such as tricyclohexylphosphine and tri-tert-butylphosphine).

The phosphines may be in oxide form.

Examples of the oxide form include di(cyclo)alkylphosphine oxides (e.g., di-tert-butylphosphine oxide and di(1-adamantyl)phosphine oxide).

Arylphosphines for heterogeneous catalysts, in which a phosphine unit is introduced into a polymer chain, can also be preferably used.

Specific examples thereof include triarylphosphine shown in the chemical formula below; i.e., one of the phenyl groups of triphenylphosphine is bound to a polymer chain.

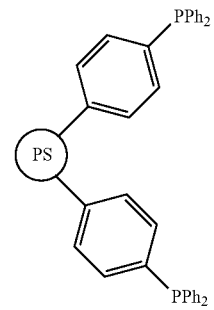

Examples of the diamines include tetramethylethylenediamine and 1,2-diphenylethylenediamine.

Examples of the bipyridines include 2,2'-bipyridyl, 4,4'-dimethyl-2,2'-bipyridyl, 5,5'-dimethyl-2,2'-bipyridyl, 6,6'-dimethyl-2,2'-bipyridyl, 4,4'-di-tert-butyl-2,2'-bipyridine, 4,4'-dimethoxy-2,2'-bipyridyl, 2,2'-biquinoline, and α,α',α"-tripyridyl.

Examples of the phenanthrolines include 1,10-phenanthroline, 2-methyl-1,10-phenanthroline, 3-methyl-1,10-phenanthroline, 5-methyl-1,10-phenanthroline, 2,9-dimethyl-1,10-phenanthroline, 2,9-diphenyl-1,10-phenanthroline, 4,7-dimethyl-1,10-phenanthroline, 5,6-dimethyl-1,10-phenanthroline, 4,7-diphenyl-1,10-phenanthroline, 2,9-dimethyl-4,7-diphenyl-1,10-phenanthroline, and 3,4,7,8-tetramethyl-1,10-phenanthroline.

Preferred examples of the ligands include phosphines, diamines, bipyridines, and phenanthrolines.

More preferable examples of the ligands include triarylphosphines and tri(cyclo)alkylphosphines.

Preferred examples of triarylphosphines include triphenylphosphine and tris[3,5-bis(trifluoromethyl)phenyl]phosphine.

Preferred examples of tri(cyclo)alkylphosphines include tricyclohexylphosphine, tri-tert-butylphosphine, triisopropylphosphine, and tri(1-adamantyl)phosphine.

Preferred examples thereof also include triarylphosphines formed by binding one of the phenyl groups of triphenylphosphine to a polymer chain as described above.

Specific preferable examples of the palladium catalyst include tris(benzylideneacetone)dipalladium and bis(benzylideneacetone)palladium.

Coordination Compound

The reaction of step A can preferably be performed in the presence of a coordination compound.

That is, the reaction of step A can be preferably performed in the presence of the transition metal catalyst mentioned above and a coordination compound.

The coordination compound used in step A is a compound capable of forming a coordinate bond with the transition metal catalyst (e.g., palladium).

Examples of the coordination compound include the examples of the ligand mentioned above.

The coordination compound is particularly preferably a biphenyl compound represented by formula (4-1):

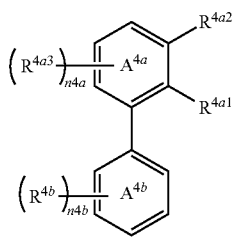

(4-1)

wherein
$A^{4a}$ is a benzene ring,
$A^{4b}$ is a benzene ring,
$R^{4a1}$ is a phosphino group substituted with two $C_{1-20}$ hydrocarbon groups,
$R^{4a2}$ is an alkyl group or an alkoxy group,
$R^{4a3}$, in each occurrence, is the same or different and represents a substituent,
$R^{4b}$, in each occurrence, is the same or different and represents a substituent,
n4a is a number of 0 to 3, and
n4b is a number of 0 to 5.

$R^{4a1}$ is
preferably a phosphino group substituted with two substituents (which may be the same or different) selected from the group consisting of secondary $C_{1-6}$ alkyl, tertiary $C_{1-6}$ alkyl, and $C_{3-12}$ cycloalkyl groups,
more preferably a phosphino group substituted with two substituents (which may be the same or different) selected from the group consisting of isopropyl, cyclohexyl, tert-butyl, and adamantyl groups,
still more preferably a phosphino group substituted with two substituents (which may be the same or different) selected from the group consisting of cyclohexyl, tert-butyl, and adamantyl groups, and
even more preferably a phosphino group substituted with two substituents (which may be the same or different) selected from the group consisting of tert-butyl and adamantyl groups.

$R^{4a2}$ is
preferably a $C_{1-6}$ alkyl group or a $C_{1-6}$ alkoxy group, more preferably an isopropyl group, a methyl group, an ethyl group, a methoxy group, or an ethoxy group,
still more preferably a methyl group, an ethyl group, a methoxy group, or an ethoxy group, and
even more preferably a methyl group or a methoxy group.

It is preferable that
$R^{4a1}$ be a phosphino group substituted with two substituents selected from the group consisting of cyclohexyl, tert-butyl, and adamantyl groups, and
$R^{4a2}$ be a methyl group or a methoxy group.

$R^{4a3}$, in each occurrence, is the same or different and preferably represents a $C_{1-6}$ alkyl group, a $C_{1-6}$ alkoxy group, or di($C_{1-6}$ alkyl)amino, and
more preferably represents a methyl group, an ethyl group, an isopropyl group, a cyclohexyl group, a tert-butyl group, a methoxy group, an ethoxy group, an isopropoxy group, or a dimethyl amino group.

$R^{4b}$, in each occurrence, is the same or different and represents a substituent,
preferably a $C_{1-6}$ alkyl group, a $C_{1-6}$ alkoxy group, or a di($C_{1-6}$ alkyl)amino, and
more preferably a methyl group, an ethyl group, an isopropyl group, a cyclohexyl group, a tert-butyl group, a methoxy group, an ethoxy group, an isopropoxy group, or a dimethyl amino group.

n4a is
preferably 0 to 3,
more preferably 1 to 2, and
still more preferably 1.

n4b is
preferably 0 to 5,
more preferably 1 to 4, and
still more preferably 2 to 3.

In a preferable embodiment,
$A^{4a}$ is a benzene ring,
$A^{4b}$ is a benzene ring,
$R^{4a1}$ is a phosphino group substituted with two identical or different $C_{1-10}$ hydrocarbon groups,
$R^{4a2}$ is a methyl group or a methoxy group,
$R^{4a3}$, in each occurrence, is the same or different and represents a methyl group or a methoxy group,
$R^{4b}$, in each occurrence, is the same or different and represents an isopropyl group,
n4a is a number of 1 to 3, and
n4b is a number of 2 to 3.

In a more preferable embodiment,
$A^{4a}$ is a benzene ring,
$A^{4b}$ is a benzene ring,
$R^{4a1}$ is a phosphino group substituted with two substituents (which may be the same or different) selected from the group consisting of secondary $C_{1-6}$ alkyl, tertiary $C_{1-6}$ alkyl, and $C_{3-12}$ cycloalkyl groups,
$R^{4a2}$ is a methyl group or a methoxy group,
$R^{4a3}$, in each occurrence, is the same or different and represents a methyl group or a methoxy group,
$R^{4b}$, in each occurrence, is the same or different and represents an isopropyl group,
n4a is a number of 1 to 3, and
n4b is a number of 2 to 3.

In a still more preferable embodiment,
$A^{4a}$ is a benzene ring,
$A^{4b}$ is a benzene ring,
$R^{4a1}$ is a phosphino group substituted with two substituents selected from the group consisting of cyclohexyl, tert-butyl, and adamantyl groups,
$R^{4a2}$ is a methoxy group,
$R^{4a3}$, in each occurrence, is the same or different and represents a methyl group or a methoxy group,
$R^{4b}$, in each occurrence, is the same or different and represents an isopropyl group,
n4a is 1, and
n4b is 3.

Preferable examples of the coordination compounds include 2-(dicyclohexylphosphino)-3,6-dimethoxy-2',4',6'-triisopropyl-1,1'-biphenyl, 2-(di-tert-butylphosphino)-2',4',6'-triisopropyl-3,6-dimethoxy-1,1'-biphenyl, 2-(di-tert-butylphosphino)-3-methoxy-6-methyl-2',4',6'-triisopropyl- 1,1'-biphenyl, and (3R,5R)-adamantan-1-yl(3S,5-adamantan-1-yl)(2',4',6'-triisopropyl-3,6-dimethoxy-(1,1'-biphenyl)-2 yl)phosphine.

Base

The reaction of step A can preferably be performed in the presence of a base.

That is, the reaction of step A can preferably be performed in the presence of the transition metal catalyst mentioned above and a base.

The reaction of step A can preferably be performed in the presence of the transition metal catalyst mentioned above, the coordination compound mentioned above, and a base.

The base is preferably a base having a pKa of preferably 36 to 3.6, more preferably 20 to 5, and even more preferably 12 to 9.

In the present specification, pKa refers to a numerical value determined by performing acid-base titration in water at 25° C. When a basic compound has multiple pKa values, the maximum value is taken as the pKa value of the basic compound.

The base is preferably at least one member selected from the group consisting of
(1) acetates, carbonates, hydrogen carbonates, phosphates, hydrogen phosphates, alkoxide salts, hydroxide salts, hydride salts, ammonium salts, or amide salts of alkaline or alkaline earth metals, or combinations of two or more of these,
(2) polymer-supported bases,
(3) alkali metals, and
(4) amines.

Examples of the alkoxide salts include sodium methoxide, sodium ethoxide, sodium butoxide, potassium methoxide, potassium ethoxide, potassium butoxide, lithium methoxide, and lithium ethoxide.

Examples of the hydroxide salts include sodium hydroxide, potassium hydroxide, lithium hydroxide, rubidium hydroxide, cesium hydroxide, magnesium hydroxide, calcium hydroxide, and barium hydroxide.

Examples of the hydride salts include sodium hydride, potassium hydride, lithium hydride, and calcium hydride.

Examples of the polymer-supported bases include Amberlite (trade name) resin.

Examples of the alkali metals include sodium, potassium, and lithium.

Examples of the amines include aliphatic amines, alicyclic amines, aromatic amines, and heterocyclic amines. The amines can preferably be tertiary amines.

The base is preferably at least one member selected from the group consisting of sodium hydrogen carbonate, potassium hydrogen carbonate, sodium carbonate, potassium carbonate, cesium carbonate, sodium acetate, potassium acetate, trimethylamine, triethylamine, pyridine, sodium methoxide, potassium methoxide, sodium tert-butoxide, potassium tert-butoxide, lithium hexamethyldisilazide, and lithium diisopropylamide.

The base is particularly preferably cesium carbonate.

The amount of the palladium catalyst used in step A may be preferably 0.001 to 0.3 mol, more preferably 0.002 to 0.1 mol, and even more preferably 0.003 to 0.05 mol, per mole of compound (2).

The target product is efficiently obtained by performing the reaction using a palladium catalyst in this amount range.

The amount of the coordination compound used in step A may be preferably 0.002 to 0.6 mol, more preferably 0.004 to 0.2 mol, and even more preferably 0.006 to 0.1 mol, per mole of compound (2).

The target product is efficiently obtained by performing the reaction using a coordination compound in this amount range.

The amount of the weak base used in step A may be preferably 0.5 to 5 mol, more preferably 1 to 3 mol, and even more preferably 1.2 to 2 mol, per mole of compound (2).

The target product is efficiently obtained by performing the reaction using a weak base in this amount range.

The amount of compound (3) used in step A may be preferably 0.05 to 10 mol, more preferably 0.08 to 5 mol, and even more preferably 0.1 to 2 mol, per mole of compound (2).

The target product is efficiently obtained by performing the reaction using compound (3) in this amount range.

The reaction can be performed in the presence or absence of an inert gas (e.g., nitrogen gas).

The reaction of step A can be performed in the presence of or absence of a solvent.

Examples of the solvent include aprotic solvents.

Examples of the aprotic solvent include aromatic hydrocarbons, such as benzene, toluene, and xylene; ethers, such as cyclopentyl methyl ether, tetrahydrofuran, dimethoxyethane, bis(2-methoxyethyl)ether, triethylene glycol dimethyl ether, and 1,2-bis(2-methoxyethoxy)ethane; lactams, such as N-methylpyrrolidone;
nitriles, such as acetonitrile and propionitrile;
ketones, such as acetone, ethyl methyl ketone, and isobutyl methyl ketone;
dialkyl sulfoxides, such as dimethyl sulfoxide;
tetraalkylureas, such as 1,3-dimethyl-2-imidazolidinone, dimethylpropyleneurea, and tetramethylurea;
amides, such as N,N-dimethylformamide, N,N-dimethylacetamide, and hexaalkylphosphoric triamide (e.g., hexamethylphosphoric acid amide).

These solvents may be used alone, or in a combination of two or more.

The amount of the solvent for use can be determined to be an amount that is sufficient for the solvent to exhibit its function based on common technical knowledge.

The upper limit of the reaction temperature in step A can be preferably 200° C., more preferably 150° C., and even more preferably 120° C.

The lower limit of the reaction temperature in step A can be preferably 25° C., more preferably 50° C., and even more preferably 90° C.

The reaction temperature in step A can be preferably 25 to 200° C., more preferably 50 to 150° C., and even more preferably 90 to 120° C.

The lower the upper limit of the reaction temperature in step A, the more likely it is that side reactions can be suppressed.

The higher the lower limit of the reaction temperature in step A, the more likely it is that the progress of the desired reaction is promoted.

The upper limit of the reaction time in step A can be preferably 48 hours, more preferably 24 hours, and even more preferably 12 hours.

The lower limit of the reaction time in step A can be preferably 0.5 hours, more preferably 2 hours, and even more preferably 6 hours.

The reaction time in step A can be preferably 0.5 to 48 hours, more preferably 2 to 24 hours, and even more preferably 6 to 12 hours.

The shorter the upper limit of the reaction time in step A, the more likely it is that side reactions can be suppressed.

The longer the lower limit of the reaction time in step A, the more likely it is that the progress of the desired reaction is promoted.

The reaction of step A can be performed in the presence or absence of an inert gas (e.g., nitrogen gas).

The reaction of step A can preferably be performed in the presence of an inert gas (e.g., nitrogen gas).

Step A can be performed under reduced pressure, atmospheric pressure, or increased pressure.

According to the production method of the present disclosure, the molar yield of the compound (1) with respect to compound (2) can preferably be 50% or more, more preferably 60% or more, even more preferably 70% or more, and still more preferably 80% or more.

The compound (1) obtained in step A can be isolated or purified by a known method, such as extraction, dissolution, concentration, precipitation, dehydration, adsorption, distillation, rectification, or chromatography; or combinations thereof, if desired.

2. Compound

Among the compounds that can be produced by the production method described above, the following compounds are novel compounds.

The present disclosure also provides the following compounds.

The following compounds can be usefully used, for example, as a monomer for polymer production, a pharmaceutical intermediate, or a pesticide intermediate.

Preferable examples of substituents and moieties of the following compounds may be understood with reference to the descriptions above for the production method.

Compounds represented by formula (1):

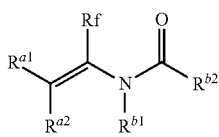

(1)

wherein
Rf is —F or fluoroalkyl,
$R^{a1}$ is —H or an organic group, and
$R^{a2}$ is —H or an organic group, or
(i) $R^{a1}$ and $R^{a2}$, (ii) $R^{a1}$ and Rf, or (iii) Rf and $R^{a2}$, may be linked to each other,
$R^{b1}$ is —H or an organic group, and
$R^{b2}$ is —H or an organic group, or
$R^{b1}$ and $R^{b2}$ may be linked together with their adjacent atoms to form a nitrogen-containing ring optionally substituted with one or more substituents, with the proviso that substituted benzimidazole is excluded, with the proviso that when $R^{a1}$ or $R^{a2}$, or both, are hydrogen, $R^{b2}$ is not a mono- or di-substituted amino group.

Although preferable examples of these compounds are understandable from the descriptions above for the production method, the following further describes such compounds.

In formula (1), it is preferred that
$R^{a1}$ be —H,
$R^{a2}$ be —H,
$R^{b1}$ be -$L^b$-$R^h$, and
$R^{b2}$ be -$L^b$-$R^h$,
wherein $R^h$, in each occurrence, independently represents an aliphatic hydrocarbyl group optionally substituted with one or more substituents (one or more heteroatoms selected from the group consisting of O, S, and Si may be inserted into the aliphatic hydrocarbyl group), or an aromatic ring group optionally substituted with one or more substituents, and
$L^b$ is a single bond, —O—, or —S—.

In formula (1), it is more preferred that either $R^{a1}$ or $R^{a2}$ be —H, and
the other be —H or an aromatic ring group optionally substituted with one or more substituents.

In formula (1), it is still more preferred that $R^{a1}$ and $R^{a2}$ each independently represent an organic group.

In formula (1), it is even more preferred that $R^{b1}$ and $R^{b2}$ be linked together with their adjacent atoms to form a nitrogen-containing heterocyclic ring optionally substituted with one or more substituents.

Although embodiments are described above, it can be understood that various modifications in form and details may be made without departing from the spirit and scope of the claims.

The elements, forms, and details of one embodiment disclosed in the present specification may be replaced and/or added to elements, forms, and details of other embodiments, without departing from the spirit and scope of the claims.

EXAMPLES

The present disclosure is described in more detail below with reference to Examples. However, the present disclosure is not limited to the Examples.

The meanings of the symbols and abbreviations in the Examples are shown below.

Example 1

Synthesis of 1-(1-fluorovinyl)pyrrolidin-2-one

Tris(benzylideneacetone)dipalladium (11.0 mg), 2-(di-tert-butylphosphino)-2',4',6'-triisopropyl-3,6-dimethoxy-1,1'-biphenyl (14.5 mg), 2-pyrrolidone (85.1 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C. 1-1-bromo-1-fluoroethylene (200 mg) was added to the container.

The container was heated at 110° C. for 18 hours.

After cooling the container to room temperature, the contents of the pressure-resistant container were filtered through Celite with dichloromethane and analyzed by $^{19}$F NMR, which revealed the production of the target title vinylamide with a molar yield of 66% with respect to 2-pyrrolidone (NMR).

Example 2

Synthesis of 1-(1-fluorovinyl)pyrrolidin-2-one

Tris(benzylideneacetone)dipalladium (11.0 mg), 2-(di-tert-butylphosphino)-2',4',6'-triisopropyl-3,6-dimethoxy-1,1'-Biphenyl (14.5 mg), 2-pyrrolidone (85.1 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C., 1-chloro-1-fluoroethylene (720 mg) was added to the container.

The container was heated at 110° C. for 18 hours.

After cooling the container to room temperature, the contents of the pressure-resistant container were filtered through Celite with dichloromethane and analyzed by $^{19}$F NMR, which revealed the production of the target title vinylamide with a molar yield of 98% with respect to 2-pyrrolidone (NMR).

Example 3

Synthesis of 1-(1-fluorovinyl)piperidin-2-one

Tris(benzylideneacetone)dipalladium (11.0 mg), 2-(di-tert-butylphosphino)-2',4',6'-triisopropyl-3,6-dimethoxy-1,1'-biphenyl (14.5 mg), 2-piperidone (99.1 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C., 1-chloro-1-fluoroethylene (400 mg) was added to the container.

The container was heated at 110° C. for 18 hours.

After the container was cooled to room temperature, the contents of the pressure-resistant container were filtered through Celite with dichloromethane and analyzed by $^{19}$F NMR, which revealed the production of the target title vinylamide with a molar yield of 48% with respect to 2-piperidone (NMR).

Example 4

Synthesis of 2-(1-fluorovinyl)isoindolin-1-one

Tris(benzylideneacetone)dipalladium (11.0 mg), 2-(di-tert-butylphosphino)-2',4',6'-triisopropyl-3,6-dimethoxy-1,1'-biphenyl (14.5 mg), isoindolin-1-one (133 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C., 1-chloro-1-fluoroethylene (400 mg) was added to the container.

The container was heated at 110° C. for 18 hours.

After cooling the container to room temperature, the contents of the pressure-resistant container were filtered through Celite with dichloromethane and analyzed by $^{19}$F NMR, which revealed the production of the target title vinylamide with a molar yield of 76% with respect to isoindolin-1-one (NMR).

Example 5

Synthesis of 3-(1-fluorovinyl)oxazolidin-2-one

Tris(benzylideneacetone)dipalladium (11.0 mg), 2-(di-tert-butylphosphino)-2',4',6'-triisopropyl-3,6-dimethoxy-1,1'-biphenyl (14.5 mg), oxazolidin-2-one (87.1 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C., 1-chloro-1-fluoroethylene (400 mg) was added to the container.

The container was heated at 110° C. for 18 hours.

After cooling the container to room temperature, the contents of the pressure-resistant container were filtered through Celite with dichloromethane and analyzed by $^{19}$F NMR, which revealed the production of the target title vinylamide with a molar yield of 91% with respect to oxazolidin-2-one (NMR).

Example 6

Synthesis of N-(1-fluorovinyl)-N-methylbenzamide

Tris(benzylideneacetone)dipalladium (11.0 mg), 2-(di-tert-butylphosphino)-2',4',6'-triisopropyl-3,6-dimethoxy-1,1'-biphenyl (14.5 mg), N-methylbenzamide (135 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C., 1-chloro-1-fluoroethylene (300 mg) was added to the container.

The container was heated at 110° C. for 18 hours.

After cooling the container to room temperature, the contents of the pressure-resistant container were filtered through Celite with dichloromethane and analyzed by $^{19}$F NMR, which revealed the production of the target title vinylamide with a molar yield of 27% with respect to N-methylbenzanide (NMR).

Example 7

Synthesis of 1-(3,3,3-trifluoro-1-propen-2-yl)pyrrolidin-2-one

Tris(benzylideneacetone)dipalladium (11.0 mg), 2-(di-tert-butylphosphino)-2',4',6'-triisopropyl-3,6-dimethoxy-1,1'-biphenyl (14.5 mg), 2-pyrrolidone (85.1 mg), and cesium carbonate (489 mg) were placed in a 10-mL pressure-resistant container. The container was hermetically sealed and purged with nitrogen.

Dimethoxyethane (2 mL) was added to the container in a nitrogen atmosphere.

After cooling the container to −78° C., 2-chloro-3,3,3-trifluoropropene (280 mg) was added to the container.

The container was heated at 110° C. for 18 hours.

After the container was cooled to room temperature, the contents of the pressure-resistant container were filtered through Celite with dichloromethane and analyzed by $^{19}$F NMR, which revealed the production of the target title vinylamide with a molar yield of 22% (isomer ratio 1:1.3) with respect to 2-pyrrolidone (NMR).

Example 8

Synthesis of 1-[2-(1,1'-biphenyl-4-yl)-1-fluorovinyl]pyrrolidin-2-one

Tris(benzylideneacetone)dipalladium (4.9 mg), 2-(dicyclohexylphosphino)-3,6-dimethoxy-2',4',6'-triisopropyl-1,1'-biphenyl (6.4 mg), 4-(2-bromo-2-fluorovinyl)-1,1'-biphenyl (150 mg), and cesium carbonate (264 mg) were placed in a 10-mL two-necked test tube. The container was hermetically sealed and purged with nitrogen.

Toluene (1 mL) and 2-pyrrolidone (55.3 mg) were added to the container in a nitrogen atmosphere.

The container was heated at 110° C. for 6 hours.

After the container was cooled to room temperature, the contents of the container were filtered through Celite with dichloromethane and purified by silica gel column chromatography. The results revealed the production of the target title vinylamide with a molar yield of 91% with respect to 4-(2-bromo-2-fluorovinyl)-1,1'-biphenyl.

The invention claimed is:

1. A method for producing a compound represented by formula (1):

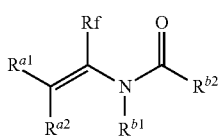

(1)

wherein
Rf is -F or fluoroalkyl,
$R^{a1}$ is -H or an organic group, and
$R^{a2}$ is -H or an organic group, or
(i) $R^{a1}$ and $R^{a2}$, (ii) $R^{a1}$ and Rf, or (iii) Rf and $R^{a2}$, may be linked to each other,
$R^{b1}$ is -H or an organic group, and
$R^{b2}$ is -H or an organic group, or
$R^{b1}$ and $R^{b2}$ may be linked together with their adjacent atoms to form a nitrogen-containing ring optionally substituted with one or more substituents,
the method comprising
step A of reacting a compound represented by formula (2):

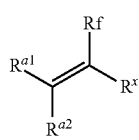

(2)

wherein
$R^x$ is a leaving group, and other symbols are as defined above,
with
a compound represented by formula (3) or a salt thereof:

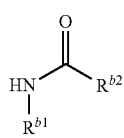

(3)

wherein the symbols in the formula are as defined above, in the presence of a transition metal catalyst.

2. The production method according to claim 1, wherein Rf is -F or perfluoroalkyl.

3. The production method according to claim 1, wherein $R^{a1}$ is -H, an alkyl group optionally substituted with one or more substituents, or an aromatic ring group optionally substituted with one or more substituents.

4. The production method according to claim 1, wherein $R^{a2}$ is -H, an alkyl group optionally substituted with one or more substituents, or an aromatic ring group optionally substituted with one or more substituents.

5. The production method according to claim 1, wherein either $R^{a1}$ or $R^{a2}$ is -H, and the other is -H or an aromatic ring group optionally substituted with one or more substituents.

6. The production method according to claim 1, wherein $R^x$ is a halo group or a sulfonic acid ester group.

7. The production method according to claim 1,
wherein
$R^{b1}$ is -$L^b$-$R^h$,
wherein
$R^h$ is
an aliphatic hydrocarbyl group optionally substituted with one or more substituents, wherein one or more heteroatoms selected from the group consisting of O, S, and Si may be inserted into the aliphatic hydrocarbyl group, or
an aromatic ring group optionally substituted with one or more substituents, and $L^b$ is a single bond,-$NR^r$-,-O-, or -S-, and $R^r$ is -H or an alkyl group.

8. The production method according to claim 1,
wherein
$R^{b2}$ is -$L^b$-$R^h$,
wherein
$R^h$ is
an aliphatic hydrocarbyl group optionally substituted with one or more substituents, wherein one or more heteroatoms selected from the group consisting of O, S, and Si may be inserted into the aliphatic hydrocarbyl group, or
an aromatic ring group optionally substituted with one or more substituents, and $L^b$ is a single bond,-$NR^r$-,-O-, or -S-, and $R^r$ is -H or an alkyl group.

9. The production method according to claim 8, wherein $R^{b1}$ and $R^{b2}$ are linked together with their adjacent atoms to form a nitrogen-containing heterocyclic ring optionally substituted with one or more substituents.

10. The production method according to claim 1, wherein the transition metal catalyst is at least one member selected from the group consisting of palladium catalysts, copper catalysts, nickel catalysts, platinum catalysts, and iron catalysts.

11. The production method according to claim 1, wherein the transition metal catalyst is at least one member selected from the group consisting of palladium catalysts, copper catalysts, and nickel catalysts.

12. The production method according to claim 1, wherein the transition metal catalyst is a palladium catalyst.

13. The production method according to claim 1, wherein the reaction of step A is performed in the presence of a coordination compound.

14. The production method according to claim 13,
wherein
the coordination compound is a biphenyl compound represented by formula (4-1):

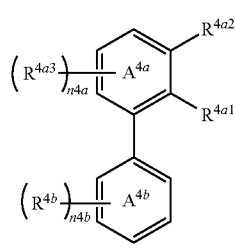

(4-1)

wherein

A$^{4a}$ is a benzene ring,

A$^{4b}$ is a benzene ring,

R$^{4a1}$ is a phosphino group substituted with two C$_{1-20}$ hydrocarbyl groups, R$^{4a2}$ is an alkyl group or an alkoxy group, R$^{4a3}$, in each occurrence, is the same or different and represents a substituent, R$^{4b}$, in each occurrence, is the same or different and represents a substituent, n4a is a number of 0 to 3, and n4b is a number of 0 to 5.

15. The production method according to claim 13, wherein the coordination compound is a biphenyl compound represented by formula (4-1):

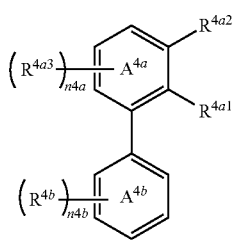

(4-1)

wherein

A$^{4a}$ is a benzene ring,

A$^{4b}$ is a benzene ring,

R$^{4a1}$ is a phosphino group substituted with two substituents selected from the group consisting of cyclohexyl, tert-butyl, and adamantyl groups, R$^{4a2}$ is a methyl group or a methoxy group, R$^{4a3}$, in each occurrence, is the same or different and represents a substituent, R$^{4b}$, in each occurrence, is the same or different and represents a substituent, n4a is a number of 0 to 3, and n4b is a number of 0 to 5.

16. The production method according to claim 1, wherein the reaction of step A is performed in the presence of a base.

17. The production method according to claim 16, wherein the base has a pKa of 36 to 3.6.

18. The production method according to claim 16, wherein the base is at least one member selected from the group consisting of (1) acetates, carbonates, hydrogen carbonates, phosphates, hydrogen phosphates, alkoxide salts, hydroxide salts, hydride salts, ammonium salts, or amide salts of alkaline or alkaline earth metals, (2) polymer-supported bases, (3) alkali metals, and (4) amines.

* * * * *